United States Patent [19]

Blackmer et al.

[11] Patent Number: 4,722,334

[45] Date of Patent: Feb. 2, 1988

[54] METHOD AND APPARATUS FOR PULMONARY AND CARDIOVASCULAR CONDITIONING OF RACEHORSES AND COMPETITION ANIMALS

[75] Inventors: Richard H. Blackmer, Scotia; Jonathan W. Hedman, Burnt Hills, both of N.Y.

[73] Assignee: Transpirator Technologies, Inc., Somerset, N.J.

[21] Appl. No.: 755,562

[22] Filed: Jul. 16, 1985

[51] Int. Cl.⁴ .............................................. A61M 16/00
[52] U.S. Cl. .......................... 128/203.16; 128/203.17; 128/203.76; 128/203.27; 128/204.17
[58] Field of Search ...................... 128/200.24, 203.16, 128/203.17, 203.26, 203.27, 203.12, 204.17, 399, 400, 402

[56] References Cited

U.S. PATENT DOCUMENTS

| | | | |
|---|---|---|---|
| 4,038,980 | 8/1977 | Fodor | 128/203.27 |
| 4,060,576 | 11/1977 | Grant | 128/203.27 |
| 4,201,204 | 5/1980 | Rinne et al. | 128/203.27 |
| 4,319,566 | 3/1982 | Hayward et al. | 128/204.17 |
| 4,369,777 | 1/1983 | Lwoff et al. | 128/204.17 |
| 4,401,114 | 8/1983 | Lwoff et al. | 128/204.17 |

Primary Examiner—Kyle L. Howell
Assistant Examiner—J. P. Lacyk
Attorney, Agent, or Firm—Kane, Dalsimer et al.

[57] ABSTRACT

A high humidity method and an apparatus are described which are useful for conditioning a pulmonary and/or a cardiovascular system in a large animal. The method broadly comprises delivering a humidified air stream at a dew point temperature greater than the environmental ambient dew point temperature to an animal's respiratory tract.

7 Claims, 6 Drawing Figures

METHOD AND APPARATUS FOR PULMONARY AND CARDIOVASCULAR CONDITIONING OF RACEHORSES AND COMPETITION ANIMALS

BACKGROUND OF THE INVENTION

1. Field of the Invention

A high-humidity method and an apparatus are described which are useful for conditioning a pulmonary and/or a cardiovascular system in a large animal. The method broadly comprises delivering a humidified air stream at a dew point temperature greater than the environmental ambient dew point temperature to an animal's respiratory tract.

2. Description of the Prior Art

The treatment of the respiratory tract of large animals with heated, humidified air is virtually unreported in both patent and technical journal literature. Large animals is a term commonly used in the art to refer to the following animals: equine, including standardbred and thoroughbred horses, bovine, and ovine species.

Respiratory therapy involving conditioning of the pulmonary and/or cardiovascular systems of large animals comprising delivering a saturated vapor/gas stream at a dew point temperature greater than the environmental ambient dew point temperature has not been found in a detailed search of the technical literature by the inventors.

Inhalation therapy involving inhalation by large animals of water-vapor-saturated air at dew point temperatures above ambient to above 110° F. while administering 300 to 400 liters per minute of such air to standardbred and thoroughbred racehorses also has not been found in a detailed search of the technical literature by the inventors.

In general, prior patent and technical art refer to the administration of medicines, anesthesia, drugs, (M.A.D.), etc., to small animals such as cats, dogs, chickens and the like for the purpose of enhancing vaccinations, etc. Water vapor reportedly has been transferred into the respiratory system of small animals at temperatures equal to or lower than the normal body temperature of the animals. Therapy treatment (i.e., other than replacement of bypassed natural humidification in anesthesia or other procedures involving tracheal intubation) of the respiratory tract of animals at dew point temperatures near or above normal core body temperatures is, to the best of the inventors' knowledge, unreported or unsuggested in the prior art literature both technical and patent wise in U.S. and foreign publications.

Incorporated herein in their entirety by reference are the following publications which described exercise induced pulmonary hemorrhage (EIPH):

*American Journal of Veterinary Research*, Volume 43, Number 7, pages 1123-1127, July 1892 entitled "Exercise Induced Pulmonary Hemorrhage in Thoroughbreds After Racing and Breezing". Corinne F. Raphel, DVM and Lawrence R. Soma. VMD.

*The Cornell Veterinarian*, Volume 74, Number 2, July 1984 entitled "Exercise-Induced Pulmonary Hemorrhage in Exercising Thoroughbreds: Preliminary Results with Pre-Exercise Medication" by Corinne Raphel Sweeney. Lawrence R. Soma, Cynthia A. Bucan and Susan G. Ray from the Department of Clinical Studies, New Bolton Center, School of Veterinary Medicine, University of Pennsylvania, Kennett Square, Pa. 19348.

SUMMARY OF THE INVENTION

A high humidity method and an apparatus are described which are useful for conditioning a pulmonary and/or a cardiovascular system in a large animal. The method broadly comprises delivering a humidified air stream at a dew point temperature greater than the environmental ambient dew point temperature to an animal's respiratory tract.

A high-humidity therapy and apparatus are described which are useful for clearing pulmonary secretions and hydrating the pulmonary tract and for increasing peripheral blood circulation before exercise of large competition animals.

The invention is particularly useful for the prevention and treatment of exercise-induced pulmonary hemorrhage in racehorses. More specifically, the invention relates to apparatus and methods wherein the humidity level in the respiratory tracts of large animals is increased by muzzle mask administration of water-vapor-saturated air to produce inspired dew point temperatures above ambient up to about 110° F. Wherein the respiratory tracts of animals are preconditioned and/or treated with vapor-phase water, tissue damage is avoided or reduced in one or more of the following areas: the bronchi, bronchioles, aveolar ducts/sacs, arterial and venous capillaries, and other areas of the respiratory system. The therapy treatment described herein reduces evaporative cooling in the respiratory system and thereby promotes compensatory peripheral blood circulation with a minimum consumption of energy reserves.

The pathophysiology of exercise-induced pulmonary hemmorrhage is believed to involve rupture and tearing of alveolar blood capillaries caused by negative air pressure and by over-expansion of unobstructed alveoli during maximum inspiratory effort. The present invention is a method to minimize negative inspiratory pressure and obstruction of bronchial connections to the alveoli by promoting the natural mucocilliary secretion and particulate-clearance action of the bronchial system by the prevention of airway water loss and by the hydration of airway surfaces through the administration to the upper respiratory tract of large animals of a substantially sterile, aerosol-free, water-vapor-saturated airstream. This method of improving pulmonary hygiene helps condition the animal to achieve its maximum oxygenation efficiency through reduction of airway obstructions and hydration of airway membranes and mucous. The method also eliminates evaporative cooling from the respiratory system and, typically, will increase metabolic heat rejection from other body surfaces by about 10 percent, and consequently, induces increased peripheral blood circulation.

Thus, the method of this invention not only conditions the pulmonary system but also serves as a pre-exercise warmup method to reduce exercise warmup and thereby save energy reserves for the race.

The veterinary respiratory therapy apparatus of the present invention is particularly adapted for application of vapor-phase water in treating the upper respiratory tract of large animals with a substantially, sterile, aerosol-free, water-vapor-saturated airstream having a substantially uniform dew point/dry bulb temperature above ambient temperature and to above 110° F. and at flow rates between 60 (or lower) and 500 (or higher) liters per minute, sufficient to match the normal peak inhalation flow rate of a typical racehorse.

The apparatus of this invention comprises a portable electric-powered air blower, means for humidifing the air stream, a flexible heated delivery tube, means for conducting the humidified air without excessive condensation to a muzzle mask and means for administering the humidified air to the nasal passages of a large animal such that the dew point temperature of the inspired air can be controlled from above ambient to above 110° F. The unified apparatus comprises elements that are relatively inexpensive, portable, and can be operated or maintained by individuals not having a high degree of technical expertise or horse-handling skill for pulmonary and cardiovascular conditioning of racehorses and other large animals.

DESCRIPTION OF THE PREFERRED EMBODIMENTS

Figure 1:
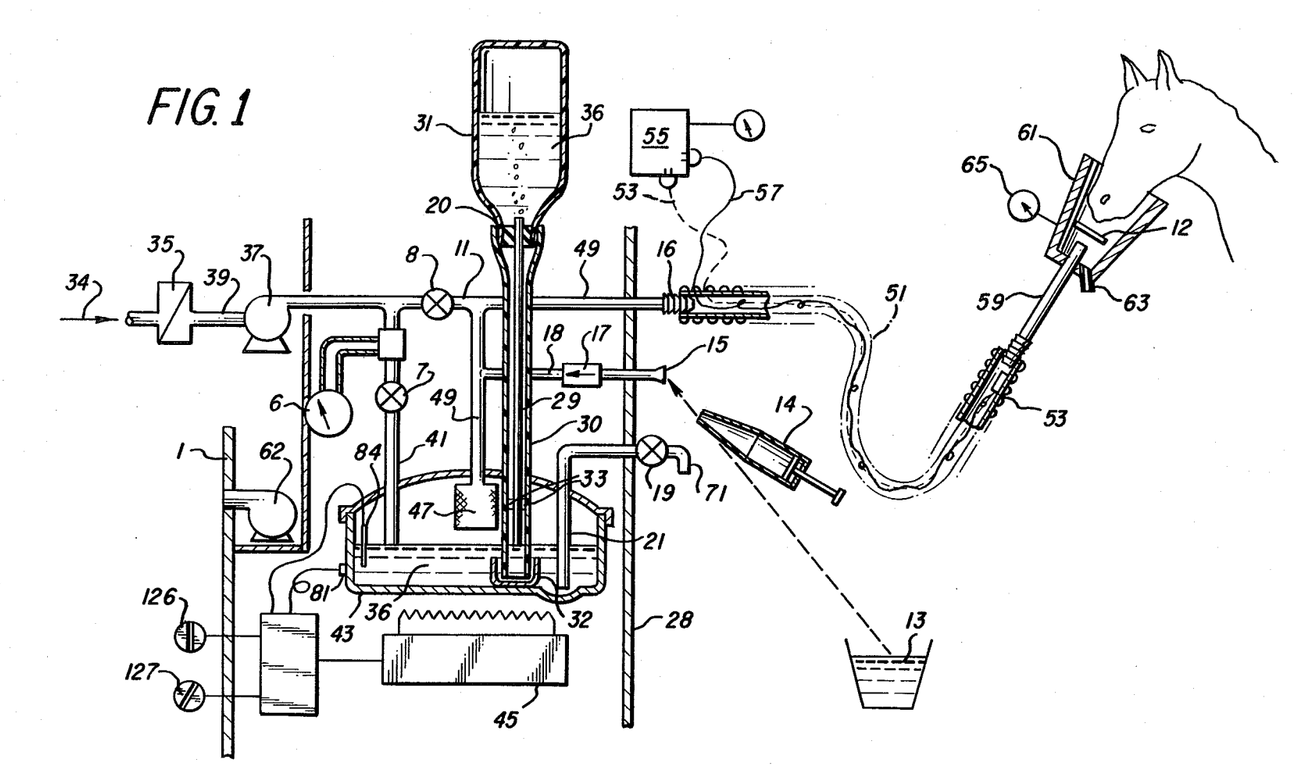
FIG. 1 is a schematic diagram of a presently preferred embodiment of the invention.

FIG. 1 is a mechanical schematic diagram of one of the presently preferred apparatuses of this invention. Ambient air 34 enters the cabinet 1 at atmospheric pressure, enters through air filter 35 and passes through to gas blower 37 via air intake line 39. The air passing from the blower 37, enters humidification pot intake line 41 under positive air pressure. The volume of air passing into the humidification pot 43 is measured by gas flow meter 6, and is controlled by air flow valve 7. This air impinges upon the liquid water 36 contained within humidification pot 43 which has been warmed by heater system 45 to the desired operative temperature which is in excess of the desired output dewpoint and preferably in excess of the temperature required for pasteurization, e.g., 140° to 180° F. The water level in the humidification pot is maintained at a constant level by liquid water from reservoir 31 which is connected to port 20. Tube 29 from reservoir 31 terminates at the surface of water 36. Water is dispensed only when the level in humidification pot 43 falls sufficiently to admit air from the pot through tube 29 to reservoir 31. To prevent freezing of water in reservoir 31 during subfreezing ambients, waste heat from heater system 45 is directed past reservoir 31. To ensure that water dispensed from reservoir 31 is raised and maintained at pasteurization temperature for sufficient time to kill any organisms that might be present, said dispensed water is directed in a labyrinth path defined by downpipe 30 and cup 32. Downpipe 30 contains vents 33 located within humidification pot 43 so as not to interfer with the lower end of tube 29 in defining water level. The volume of said labyrinth path is sufficient to provide residence time of water in the path which is greater than required pasteurization time.

Temperature of the water 36 in humidification pot 43 is maintained at a temperature which is elevated above the desired output dew point by heater 45 which administers heat to the humidification pot in response to control signals from water temperature sensor 84. In the RUN mode, this temperature can be adjusted via variable resistor 127. Should the temperature exceed a predetermined upper limit, thermal switch 81 opens thereby turning of power to heater 45, fan 62 and blower 37. The further function of said switch will become clear upon description of FIG. 2.

Humidifier bypass valve 8, normally maintained in closed position, controls air flow through a shunt path 11 which bypasses the humidification pot 43. When therapy is being administered, this valve is closed.

Heater 45 imparts sufficient energy to the water 36 in humidification pot 43 to humidify the air entering the pot via conduit 41. The velocity and direction of this entering air are such that large water droplets may form. Said droplets are coalesced by the porous membrane 47 located at the humidification pot exit port 49 so that the humidified air exiting the humidification pot 43 via conduit 49 is free of aerosol water particles that are known irritants and potential carriers of bacteria or other undesireable species. The humidified air stream conducted by conduit 49 exits the cabinet via a fitting which connects to a heated delivery tube (HDT) 51 which incorporates a heating element 57 for maintaining the temperature of the HDT and a temperature measuring/sensing element 53 for monitoring the temperature of the vapor/gas stream at the exit muzzle-mask end of the HDT. Output heater control 55 represents collectively various vapor/gas delivery control systems including variable voltage transformer, HDT power transformer, fixed resistors, electronic light switch and power light elements (all not shown individually) that interact with heating element 57. An over-temperature switch 53 which interupts power to the heated delivery tube 51 in the event of excessive temperatures is located at the muzzle-mask end of the HDT.

Regulation of the dewpoint of the high-humidity output is accomplished by controlling the temperature of water 36 by means of adjustment 127 and the output flow rate by air flow control valve 7. The dry bulb temperature of the high-humidity output is controlled by output heater control 55. A transparent section 59 near the end of the HDT allows one to observe whether or not condensation is occuring within the HDT. Temperatures and flow rates are adjusted so that a trace of condensation is observed just short of entry into muzzle mask 61 in order to ensure that the entire volume of inspired air is 100 percent saturated. Condensation within the muzzle mask 61 and secretions from the animal drain from the mask via port 63. The mask may optionally include a baffle 12 to prevent direct impingement of high velocity air on the animal and a temperature sensor/indicator 65 to continuously monitor the temperature within the muzzle mask 61 during the administration of therapy, The flow rate delivered to the animal is adjusted by valve 7 to be substantially equal to or greater than the animal's normal resting average peak inhalation rate. For horses, this value is in the range of 300 to 400 liters per minute.

Bypass valve 8 affords a method of drying the HDT. During normal operation, this valve is in a closed position. By opening bypass valve 8, most of the output flow from blower 37 will be shunted around the humidification pot 43 via conduit 11 and will contain ambient absolute humidity. The additional water carrying capacity of this air is used to dry the heated delivery tube. During such procedures, the muzzle mask is not connected to an animal.

The apparatus is disinfected before use and between animals by introducing a cold (ambient temperature) disinfecting solution 13 via syringe 14 into disinfectant port 15 while operating. Said solution disinfects the interior surfaces of exit conduit 49, exit port 16 and heated delivery tube 51 as it flushes through them. The tubing is then dried by opening bypass valve 8 while continuing to operate at normal flow rates. Muzzle mask 61 may be disinfected by washing directly with disinfectant 13 and allowing to drip dry. A check valve 17 in the disinfectant conduit 18 prevents loss of humidified air flow through disinfectant port 15 during normal operation.

Liquid drain outlet port 71 and drain valve 19 are incorporated to provide a means of removing water 36 from the apparatus prior to extended shutdown. To drain water 36, reservoir 31 is removed and port 20 plugged, drain valve 19 is opened, and apparatus is switched on in the run mode. Water 36 is forced through drain conduit 21 by the resulting positive pressure in humidification pot 43. Additional pressure may be obtained by temporarily plugging heated delivery tube 51. Conduit 21 terminates at a low point in humidification pot 43 to drain as much water as possible.

Fan 62 draws ambient into the cabinet 1 to provide feed air for filter 35 and to provide cooling for blower 62.

Figure 2:
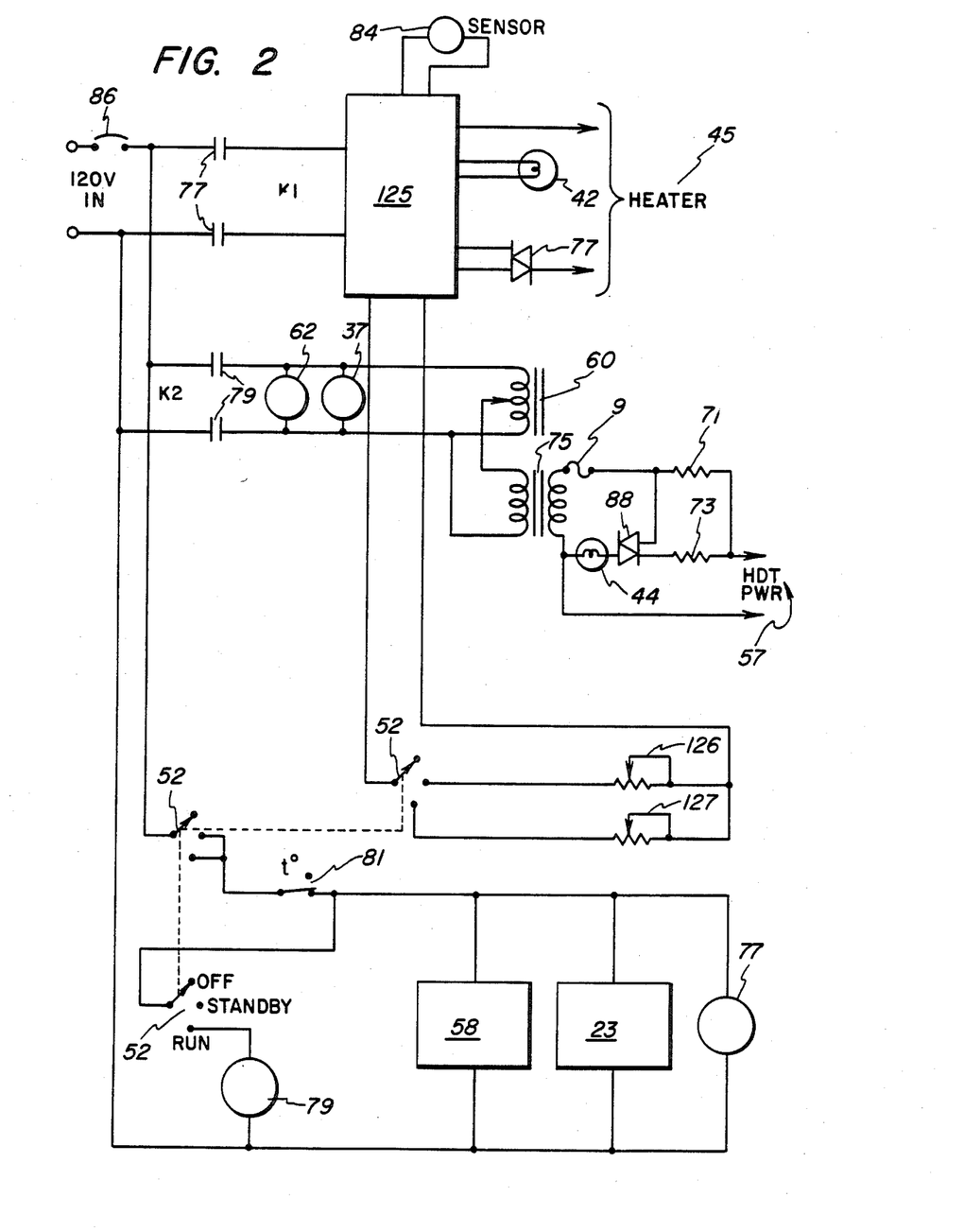
FIG. 2 is a schematic diagram of the electrical control circuit for the embodiment depicted in FIG. 1.

FIG. 2 is a preferred embodiment of the electrical system of the invention. It includes a two or three wire power supply cord (Not shown), circuit breaker 86, 3-position power switch 52, relays 77 and 79, fan 62, blower 37, digital temperature gauge 23, elapsed time indicator 58, variable voltage transformer 60, heated delivery tube transformer 75 which regulates power to heating elements (NS), a heated delivery tube fuse, heated delivery tube power light 44, fixed resistors 71 and 73, water heater temperature control printed circuit board (PCB) 125, water heater power control triac 88, water temperature sensor 84, overtemperature sensor 81, water heater power indicator light 42, and water heater 45.

Electrical power enters the apparatus through circuit breaker 86. A 3-position power switch 52 is used to set the device to OFF, STANDBY or RUN. In the OFF position, the device is not energized. In STANDBY position, digital temperature gauge 23, elapsed time indicator 58, and coil of relay K1 77 are directly energized. The contacts of relay K1 77 close to supply voltage to printed circuit 125 which controls the water heater 45 in response to a control signal from water temperature sensor 84. Variable resistor 126 is used to adjust the water temperature setpoint. The water temperature itself is read from a signal derived from a temperature sensor connected to digital temperature gauge 23. Water heater light 42 indicates whenever power is applied to water heater 45 through water heater power control triac 88. Overtemperature switch 84 is normally closed. If water temperature exceeds safe limits, it opens and interrupts all power.

In RUN position, digital temperature gauge 23, elapsed time meter 58 and coil of relay K1 77 are energized just as in the STANDBY position. However, variable resistor 127 is used to adjust water temperature. Moreover, power is supplied to the coil of relay K2 79 causing its contacts to close. This supplies power to fan 62, blower 37 and variable voltage transformer 60 which supplies power to the heated delivery tube (NS) through heated delivery tube 57 transformer 75. A fuse protects the output of this circuit against overcurrent. Resistors 71 and 73 form a divider network and act in conjunction with triac 88 to turn heated delivery tube power light 42 on whenever power beyond a threshhold value is applied to the heated delivery tube.

Figure 3:
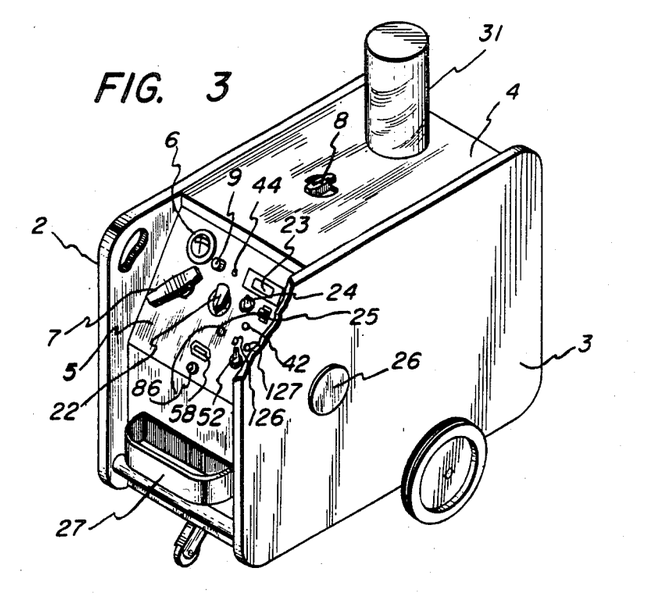
FIG. 3 is a front oblique perspective view of the portable electric powered humidifier unit of the present invention.
Figure 4:
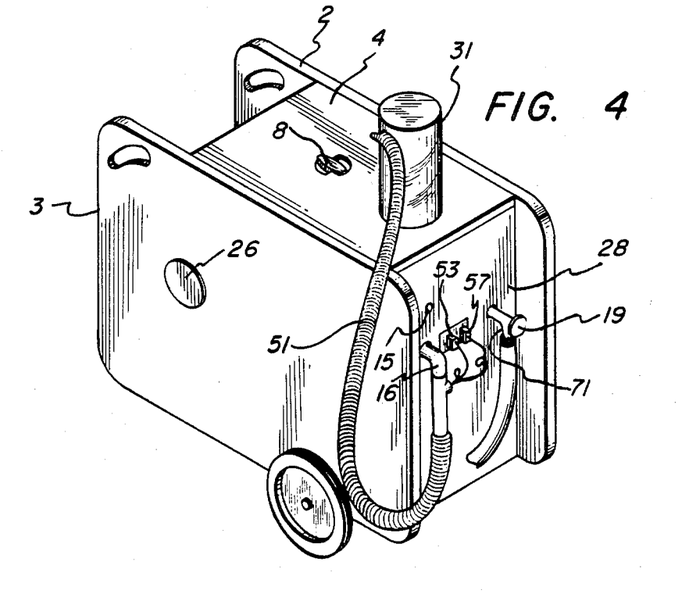
FIG. 4 is a rear oblique perspective view of the portable electric powered humidifier unit of the present invention.

The therapy apparatus of the present invention is shown by oblique perspective views in FIGS. 3 and 4. The cabinet includes left side panel 2, right side panel 3, and top panel 4, front control panel 5, and rear panel 28. Most of the controls, monitors and switches are located on the front control panel. These include: air flow valve 7, gas flow meter 6, heated delivery tube power fuse 9, heated delivery tube power light 10, digital temperature gauge 23, heated delivery tube power control 22, elapsed time meter 58, circuit breaker 86, temperature select switch 24, auxilliary sensor port 25, water heater light 42, standby temperature variable resistor 126, run temperature variable resistor 127, and power switch 52. The temperature select switch 24 is a three position rotary switch to select the temperature sensor connected to the digital temperature gauge. The three positions are: water (read temperature of water in humidifier pot (NS)), HDT (temperature at equine end of heated delivery tube and auxiliary-temperature at sensor plugged into the auxilliary sensor port). The humidifier bypass valve 8 is located on the cabinet top, as is water reservoir 31. Right panel 3 includes a port 26 to admit cooling and feed air to blower (NS). A tray 27 on the front of the apparatus provides a convenient place for the storage of disinfectant solution (Not Shown). A disinfectant syringe port 15 is located at the rear of the apparatus. Also located on the rear panel 28 are a drain port 71, drain valve 19, heated delivery tube connector 51, heated delivery tube power socket 57, and heated delivery tube temperature sensor socket 53. The heated delivery tube 51 couples to the heated delivery tube connector to provide a continuous flow path for humidified air from the apparatus to the animal. Power to the heated delivery tube is obtained by plugging into the heated delivery tube power socket. The temperature sensor socket 53 provides a means for a temperature sensor located near the animal end of the heated delivery tube to be connect to the digital temperature gauge through selection of the heated delivery tube position of temperature selector switch on the front panel. The apparatus may include integral wheels, or they may be incorporated as a separate dolly on which the apparatus rides.

Figure 5:
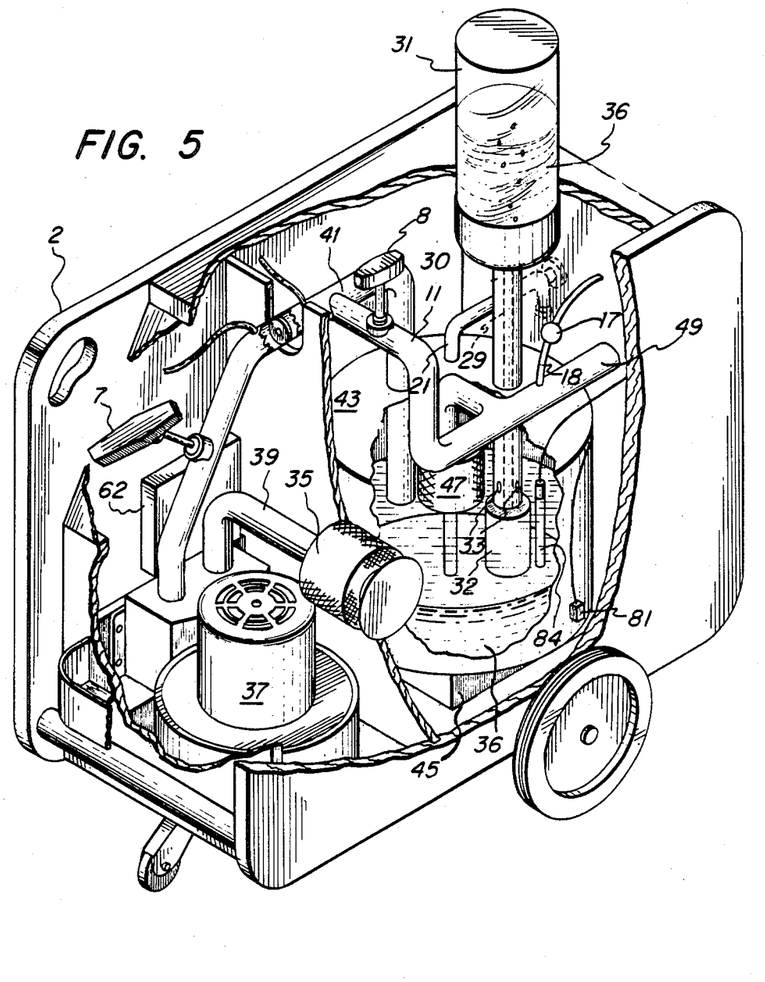
FIG. 5 is a cut-away internal sectional partial view of the humidifier unit of the therapy apparatus of the present invention.

FIG. 5 is a cut-away sectional view of the prototype of the present invention used in clinical and performance tests with racehorses. This illustration also shows a cut-away sectional view of the humidifier portion within the apparatus. Ambient air enters the cabinet 3 at atmospheric pressure, enters through air filter 35 and passes through to gas blower 37 via air intake line 39. The air passing from the blower 37, enters humidification pot intake line 41 under positive air pressure. The volume of air entering the humidification pot 43 is measured by gas flow meter (NS) and is controlled by air flow valve 7. This air impinges upon the liquid water 36 contained within humidification pot 43 which has been warmed by heater system 45 to the desired operative temperature which is in excess of the desired output dewpoint and preferably in excess of the temperature required for pasteurization, e.g., 140° to 180° F. The water level in the humidification pot is maintained at a constant level by liquid water from reservoir 31 which is connected to port (NS). A tube 29 shown in phantom dotted line mode from reservoir 31 terminates at the surface of water 36. Water is dispensed only when the level in humidification pot 43 falls sufficiently to admit air from the pot through the tube 29 to reservoir 31. To prevent freezing of water in reservoir 31 during sub-freezing ambients, waste heat from heater system 45 is directed past reservoir 31. To ensure that water dispensed from reservoir 31 is maintained at pasteurization temperature for sufficient time to kill any organisms that might be present, said dispensed water is directed in a labyrinth path defined by downpipe 30 and cup 32. Downpipe 30 contains vents 33 located above the water level so as not to interfer with the lower end of tube 29 in defining the water level. The volume of said labyrinth path is sufficient to provide residence time of water in the path which is greater than required pasteurization time.

Temperature of the water 36 in humidification pot 43 is maintained at a temperature which is elevated above the desired output dew point by heater 45 which administers heat to the humidification pot in response to control signals from water temperature sensor 84. In the RUN mode, this temperature can be adjusted. Should the temperature exceed a predetermined upper limit, a thermal switch 81 opens thereby turning off power to heater 45, fan 62 and blower 37. The further function this switch is described in FIG. 2.

Humidifier bypass valve 8, normally maintained in closed position, controls air flow through a shunt path 11 which bypasses the humidification pot 43. When therapy is being administered, this valve is closed.

Heater 45 imparts sufficient energy to the water 36 in humidification pot 43 to humidify the air entering the pot via conduit 41. The velocity and direction of this entering air are such that large water droplets may form. Said droplets are coalesced by the porous membrane 47 located at the humidification pot exit port 49 so that the humidified air exiting the humidification pot 43 via conduit 49 is free of aerosol water particles that are known irritants and potential carriers of bacteria or other undesireable species. The humidified air stream conducted by conduit 49 exits the cabinet via a fitting on the back of the cabinet (NS) which connects to a heated delivery tube.

Figure 6:
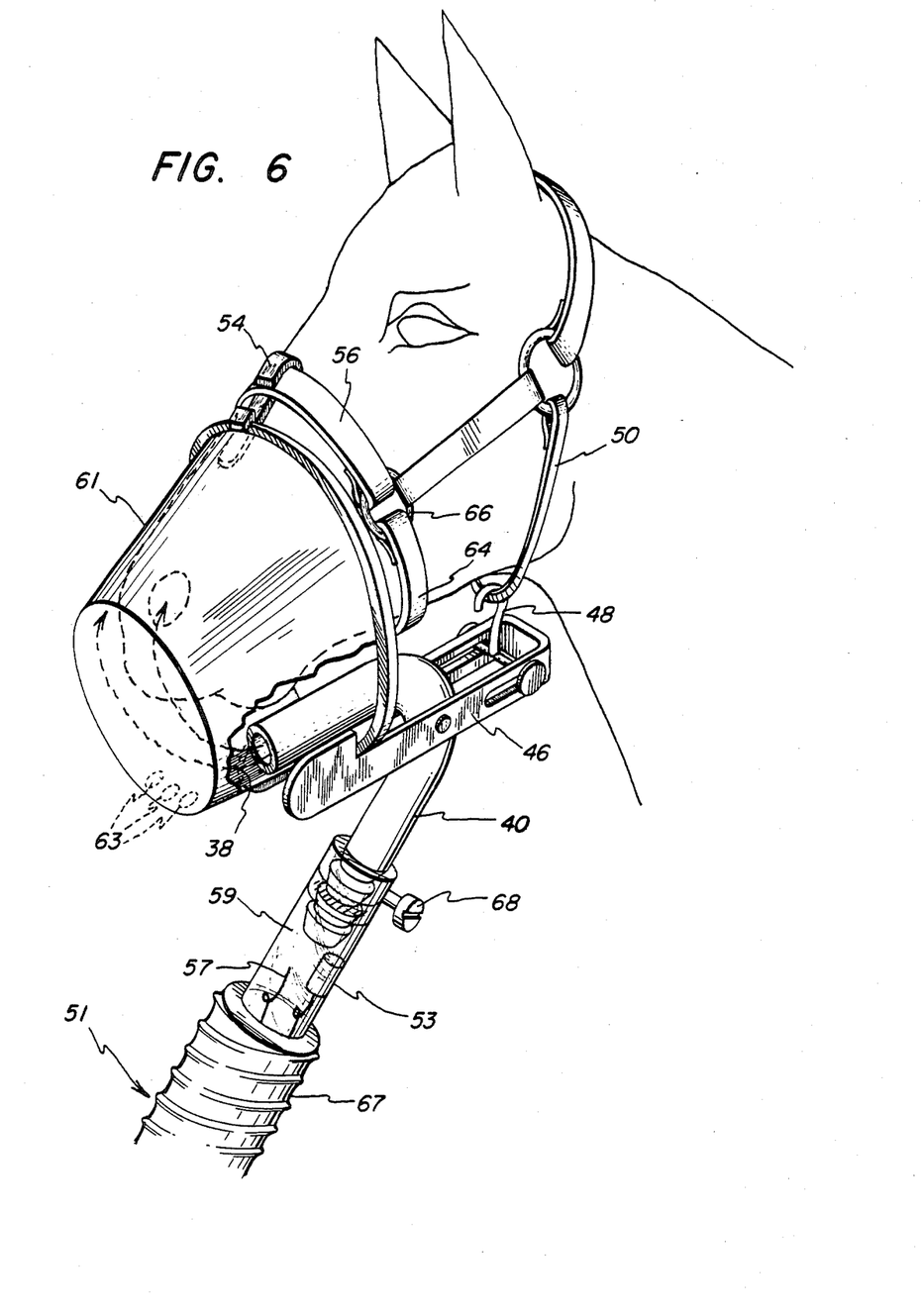
FIG. 6 is a fragmentary perspective view of a muzzle mask for the administration of a high-humidity air stream to an equine.

FIG. 6 is a fragmentary phantom view of a disposable muzzle mask for the administration of a high-humidity air stream to a horse. The high-humidity output 38 of the system is delivered to the animal by the heated delivery tube assembly 51 by way of a J-shaped tube 40 inside disposable bucket 61 which serves as an insulated muzzle mask. The animal's exhalation and any excess flow from the HDT 51 exit freely from the bucket 61 around the animal's muzzle. Any condensate from the HDT 51 and bucket 61 or secretions form the animal drain through vent ports 63. The J-shaped tube 40 serves as a finger to cooperate with the two fingers of the U-shaped bracket 46, to which it is attached, to clamp the HDT assembly to the flange of bucket 61. The clamping and release actions depend on the flexibility of the bucket 61 and of the U-shaped bracket 46. The muzzle mask assembly attaches to the animal by means of a hook 48 on the U-bracket 46 which engages the halter throat straps 50. Further security is provided by the nose hook 54 which engages the halter nose strap 56. After attachment, the horse is controlled by a halter rope (Not Shown) attached to the halter chin strap 64 or by cross ties attached to cheek rings 66.

FIG. 6 also shows more detail of the HDT assembly 51. A transparent section of the delivery tube 59 enables viewing of condensation to confirm proper operation of the system. An outer jacket 67 of spiral-corrugated plastic tubing provides thermal insulation and prevents kinking of the flexible, thin-walled delivery tube 59. Heating wires 57 provide energy to control the temperature of the high humidity output 38 as sensed by a thermocouple 53 in the air stream so as to prevent excess condensation. The delivery tube attaches to J-tube 40 by means of tubing clamps 68 which can be adjusted to provide a desired safety break-away force.

The bucket 61 can be fabricated for easy disinfection and reuse or fabricated with low-cost materials (e.g., impregnated paper) for one-time disposable use.

The following examples illustrates the high humidity therapy treatment of large animals as an effective means of preventing and/or healing, reducing, curing, repairing the tissue damage done to the cells, alveoli, mucousa, nostrils, mucus membranes, nasal passages, broncholi, etc., associated with exercise-induced pulmonary hemorrhage in horses, throughbreds and standardbreds, after racing or breezing.

The transpirator TM (respiratory therapy unit) as illustrated by FIGS. 1-6 described herein before was started and operated in accordance with the following general procedures on a 1,000 pound 5 year old standardbred mare named Oil Painting owned by Saratoga Standardbreds, Inc. having a racing history spaning from Dec. 13, 1985 to July 8, 1985. The high-humidity equine Transpirator( TM ) device was connected to 115 volt power source. The drain valve of the device was closed and the humidification water reservoir was filled with water via ambiant temperature water supply source. The power switch was turned to standby and the water heater light was turned on. The temperature select on the front panel was turned to the water bath setting and after 10 to 15 minutes, the digital temperature meter indicated a water temperature stabilization range of 135° to 155° F. The delivery tube exit gas stream conduit was disinfected by passing at least 150 ml Alcide LD 10:1:1 solution through the delivery tube into the muzzle mask while the transpirator( TM ) operated in BY-PASS mode at maximum air flow.

After disinfection of the system, the muzzle mask was brought to dew point temperature of 105° F. at the point of delivery of the saturated vapor gas to the muzzle mask attached to the horses halter. During the first treatment, Oil Painting's pulse did not exceed 40 beats per minutes and her rectal temperature did not exceed 100° F. The mare's breathing rate did not exceed 20 inspirations per minute. The liters per minute delivered to the horse and the temperatures were recorded at least once every 30 minutes, and the treatment was continued for at least two hours per day. The mare was examined after each race with a flexible fiberoptic endoscope.

The mare was raced on the date set out in the table hereafter, which also describes her position at ¾ mile point, and the position of Oil Painting at the finish of the one-mile race (1st, 2nd, 3rd, 4th, etc.), the time the mare finished, whether or not the mare had been treated before the race, and whether or not she experienced EIPH after the race.

"OIL PAINTING" BLEEDING & HIGH-HUMIDITY THERAPY HISTORY

| RACE DATE | MILE | FINISH | TIME | HHT(c) Before Race | BLEED(d) After Race |
|---|---|---|---|---|---|
| 12/13 | 3 | 2 | 2:01 | NO | NO |
| 12/20 | 4 | 2 | 2:02 | NO | NO |
| 1/2/85 | 1 | 1 | 2:03 | NO | NO |
| 1/10 | 4 | 5 | 2:01 | NO | NO |
| 2/1 | 7 | 8 | 2:06 | NO | YES |
| 2/8 | 6 | 7 | 2:07 | NO | YES |
| 2/15 | 7 | 8 | 2:04 | NO | YES |
| 2/28 | BREEZE ON FARM | | | NO | YES |
| 3/2 | 3 | 3 | 2:03 | YES | NO |
| 3/9 | 6 | 4(a) | 2:03 | YES | NO |
| 3/23 | 5 | 2(b) | 2:02 | YES | NO |
| 3/30 | 4 | 1 | 2:03 | NO | NO |
| 4/14 | 4 | 8-14 | 2:00.4 | NO | YES |
| 5/4 | 7 | 8-4 | 2:00.4 | YES | NO |
| 5/11 | 6 | 6-? | 1:59+? | YES | NO |
| 5/18 | 2 | 5-4 | 2:02.4 | YES | NO |
| 5/25 | 2 | 3-1 | 2:00.3 | YES | NO |

(a)THREE-WAY PHOTO FOR 2ND.
(b)BROKEN HARNESS AT START.
(c)1 TO 3 HOUR TREATMENTS DAILY, INCLUDING RACE DAY.
(d)ENDOSCOPE EXAM 12+ HOURS AFTER RACE.

The above chart illustrates that without humidity treatment, Oil Painting showed signs of exercised-induced pulmonary hemorrhage (EIPH) when examined with a flexible fiberoptic endoscope (FFE) 12 hours after racing on Feb. 1, 8, 15 and 28, 1985. It further illustrates that with high-humidity therapy prior to racing, Oil Painting showed no signs of EIPH in post-race FFE examination. Oil Painting was treated for two hours a day from Mar. 1, 1985 through Mar. 23, 1985, and showed no evidence of EIPH after three races in this period. Thereafter, high-humidity therapy was discontinued until after Apr. 14, 1985. She showed no evidence of EIPH after winning a race on Mar. 30, but again showed serious EIPH following a race on Apr. 14. High-humidity therapy treatment was reinitiated after the Apr. 14 race, and as illustrated by the FFE results, EIPH did not reoccur!

Oil Painting has continued treatments and racing since May 25, 1985 with steady improvement in her racing time and without EIPH. On July 8, 1985 at Meadowland, N.J., she finished third at 1:56.4 (i.e. 1 minute 56 and 4/5 seconds), the fastest mile of her career.

As of July 12, 1985 the total number of horses receiving or having received Transpirator TM treatments are as follows:

| Type | | | Disorder Treated | | |
|---|---|---|---|---|---|
| STANDARD-BRED | THOROUGH-BRED | Location | EIPH | BRONCH-ITIS | PNEU-MONIA |
| X | | Saratoga | 7 | | 1 |
| X | | Meadowlands | 4 | 4 | |
| | X | Delaware Park | 11 | 3 | |
| X | X | Univ. of PA | | | 2 |

The two horses treated for pneumonia at the University of Pennsylvania New Bolton Center were foals. Both foals responded to treatment and sought the muzzle mask voluntarily when it was hung on the wall of the stall. Veterinarians noted unexpectedly rapid recovery by one of the foals.

The other foal died of septicemia unrelated to its pneumonia. However, during one day of Transpirator TM treatment witnessed by several veterinarians, the foal sought out the muzzle mask, voluntarily placed its muzzle in the mask (standing up or lying down), and would sleep with its head in the mask without requiring straps to hold the mask on.

Four standardbred and three thoroughbred horses with severe to acute bronchitis and/or allergic polyps were given Transpirator TM conditioning treatments. Air saturated from 100° F. to 110° F. was administered by muzzle mask for about a 2-hour period at 300 to 400 liters per minute. This treatment was given once a day for three to five days in conjunction with antibiotic drug therapy. Before-and-after bronchoscope examinations revealed visible improvements in three of the horses that may be attributable to the Transpirator therapy. Three of these horses raced after treatment. Two of them posted significant improvements over their recent racing times.

Exercise-induced pulmonary hemorrhage (EIPH) has been the primary focus of Transpirator TM treatments thus far. Some 22 horses with documented or suspected EIPH have been given daily treatments for up to five days preceding a race. Each day air saturated from 100° to 110° F. was administered by muzzle mask for about a 2-hour period at 300 to 400 liters per minute. Sixteen horses raced after the treatments: none of these showed worsening of EIPH or racing performance; four showed lessening of EIPH with no change in performance; six that were not bronchoscoped showed improved performance; four showed no EIPH after racing; and three ran the best race times of their careers. Controlled studies under the supervision of University of Pennsylvania veterinarian consultants are now in progress at the Delaware Park Thoroughbred track in Newark, Del.

Other applications of Transpirator TM treatments that are planned for study in the near future include: foal and calf pneumonia, bronchitis, asthma, sinusitis, allergic rhinitis, and viral rhinitis. Several half-hour treatments at or slightly above 110° F. are expected to produce significant symptomic relief for the latter three disorders and to speed their cure. Nasal cannula administration feasibility has been demonstrated with early prototypes of the Transpirator TM for the treatment of foals and adult race horses. Nasal cannula administration permits long-term treatments without costly supervision and, since horses are obligate nasal breathers, provides a means for constant positive airway pressure (CPAP) therapy. Long-term nasal cannula administration permits an animal to suckle, drink, and eat while free-roaming on a heated delivery tube tether from the Transpirator TM, CPAP therapy opens collapsed or obstructed airways for administration of aerosolized medications and for promotion of pulmonary hygiene.

Tests are planned wherein nasal prongs with inflatable cuffed seals will be used to administer Transpirator output so as to produce CPAP or variable airway pressure to assist ventilation.

While a primary feature of the Transpirator ™ is delivery high humidity without water aerosols which might induce bronchospasms or carry pathogens into the lung, aersols of water and medication are desirable for many veterinarian treatments. The Transpirator ™ output is an ideal vehicle for aerosol medications, expecially in conjunction with nasal cannula administration. Tests are planned wherein nebulized medications will be aspirated into the Transpirator ™ output for administration by muzzle mask and nasal cannula.

We claim:

1. A high humidity method useful for conditioning a pulmonary and/or a cardiovascular system in a large veterinary animal comprising
   (i) providing a stream of gas;
   (ii) heating water in a container means;
   (iii) providing a porous membrane means disposed within said container means, said container means adapted to permit liquid droplets to contact said porous membrane surface to permit a vapor to defuse therethrough;
   (iv) mixing said vapor with said stream of gas to humidify said stream of gas;
   (v) delivering said humidified stream of gas at a rate from greater than about 60 to about 500 liters per minute to the animal's respiratory tract at a dew point temperature greater than the environmental ambient dew point temperature, said humidified air steam dew point temperature is within the range of about 99° F. to about 110° F.

2. A high humidity method of claim 1 wherein
   (i) a humidified air stream at a dew point temperature greater than the environmental ambient dew point temperature
   (ii) said humidified stream of gas is delivered in the substantial absence of nebulized water aerosol.

3. A high humidity method of claim 2 wherein
   (i) said humidified air stream is delivered at a dew point temperature greater than 93° F. (33.9° C.).

4. A claim 1 method wherein (i) the humidified air stream is delivered continously.

5. A claim 4 method wherein (i) the humidified air stream is delivered continously for a time period of less than about 24 hours.

6. A claim 5 method wherein (i) the humidified air stream is delivered continuously for a time period of less than about 8 hours.

7. A high humidity veterinary therapy method useful for conditioning pulmonary and/or cardio-vascular system in veterinary animals comprising delivering a humidified air stream at a dew point temperature within the range of about 99° F. to about 110° F. temperature and less than a permanent tissue damage temperature of an animal's central nervous system, said humidified air stream is delivered at a rate from greater than about 60 to about 500 liters per minute.

* * * * *